(12) United States Patent
Smith et al.

(10) Patent No.: US 12,070,223 B2
(45) Date of Patent: Aug. 27, 2024

(54) REPOSITIONABLE CLOSURE DEVICE

(71) Applicant: BOSTON SCIENTIFIC SCIMED, INC., Maple Grove, MN (US)

(72) Inventors: Paul Smith, Smithfield, RI (US); Kevin L. Bagley, Natick, MA (US); Ryan Evers, Billerica, MA (US); Narunn Suon, Lawrence, MA (US); James J. Scutti, Norwell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/450,803

(22) Filed: Aug. 16, 2023

(65) Prior Publication Data
US 2023/0389936 A1  Dec. 7, 2023

Related U.S. Application Data (63) Continuation of application No. 17/443,148, filed on Jul. 21, 2021, now Pat. No. 11,779,344.

(60) Provisional application No. 63/198,155, filed on Sep. 30, 2020.

(51) Int. Cl.
  *A61B 17/122* (2006.01)
  *A61B 17/00* (2006.01)
  *A61B 17/12* (2006.01)
  *A61B 17/128* (2006.01)

(52) U.S. Cl.
  CPC ........ *A61B 17/122* (2013.01); *A61B 17/1285* (2013.01); *A61B 2017/0034* (2013.01); *A61B 2017/00358* (2013.01); *A61B 2017/12004* (2013.01)

(58) Field of Classification Search
  CPC ........ A61B 2017/0034; A61B 17/1285; A61B 17/122
  See application file for complete search history.

(56) References Cited

U.S. PATENT DOCUMENTS

| | | | |
|---|---|---|---|
| 6,193,732 B1 * | 2/2001 | Frantzen | A61B 17/128 606/151 |
| 9,138,227 B2 * | 9/2015 | Schostek | A61B 5/6884 |

* cited by examiner

*Primary Examiner* — Kathleen S Holwerda
*Assistant Examiner* — Daniel Icet
(74) *Attorney, Agent, or Firm* — Fay Kaplun & Marcin, LLP (57) ABSTRACT

A closure device includes a first ring structure having a first distal portion and a first medial portion and a second ring structure having a second distal portion and a second medial portion. The first and second distal portions are movable between an open position, where the first and second distal portions form an angle relative to one another for receiving target tissue therebetween, and a closed position, where the first and second distal portions are drawn toward one another for gripping the target tissue. The device also includes an anvil about which the first and second medial portions are formed. Either one of proximal motion of the anvil relative to the first and second rings or proximal motion of the medial portions relative to the anvil causes the first and second distal portions to move into either one of the open position or the closed position.

20 Claims, 8 Drawing Sheets

REPOSITIONABLE CLOSURE DEVICE

PRIORITY CLAIM

The present application is a Continuation of U.S. patent application Ser. No. 17/443,148 filed Jul. 21, 2021; which claims priority to U.S. Provisional Patent Application Ser. No. 63/198,155 filed Sep. 30, 2020. The disclosures of the above application(s)/patent(s) are incorporated herewith by reference.

FIELD

The present disclosure relates to an endoscopic closure device actuatable between an open position and a closed position multiple times so that the device may be repositioned on target tissue.

BACKGROUND

Many endoscopic devices with distal clipping mechanisms, e.g. hemostasis clips, have a single-use quick launch mechanism. Once the clip has been closed, it is not possible to re-open and reposition the clip. If the clip is not deployed at the correct position on the target tissue there is no opportunity to reposition the clip. Additionally, many current closure devices are insufficient for certain perforations, conditions and anatomies and may be difficult to use or time-consuming in certain situations.

SUMMARY

The present disclosure relates to a closure device which includes a first ring structure having a first distal portion and a first medial portion and a second ring structure having a second distal portion and a second medial portion. The first and second distal portions are movable between an open position, where the first and second distal portions form an angle relative to one another for receiving target tissue therebetween, and a closed position, where the first and second distal portions are drawn toward one another for gripping the target tissue. The device also includes an anvil about which the first and second medial portions are formed. Either one of proximal motion of the anvil relative to the first and second rings or proximal motion of the medial portions relative to the anvil causes the first and second distal portions to move into either one of the open position or the closed position.

In an embodiment, the device further includes a locking mechanism for locking the first ring and the second ring in the closed position, the anvil including a first mechanical feature sized, shaped and positioned to engage a second mechanical feature on at least one of the first ring and the second ring when the first and second rings are in the closed position.

In an embodiment, the first mechanical feature is a locking window and the second mechanical feature is a locking tab extending from the first medial portion.

In an embodiment, the first mechanical feature is a locking window and the second mechanical feature is a locking tab extending from the second medial portion.

In an embodiment, a distal end of the first distal portion extends distally beyond a distal end of the second distal portion.

In an embodiment, the device further includes a first gripping feature extending from one of the first distal portion and the second distal portion toward the other one of the first and second distal portions.

In an embodiment, one of the first and second medial portions includes a protrusion configured to engage an end of the anvil to maintain the anvil at a desired position between the first and second medial portions.

In an embodiment, the first and second rings are biased toward the closed position.

In an embodiment, the first and second rings are biased toward the open position.

In an embodiment, the device further includes flexible connecting struts adjacent to the anvil and extending between the first medial portion of the first ring and the second medial portion of the second ring; first recesses adjacent to a first proximal portion of the first ring; and second recesses adjacent to a second proximal portion of the second ring. The first and second recesses are sized and shaped to receive the anvil therebetween.

In an embodiment, the first and second rings have a curvature at each of the first and second medial portions sized and shaped to receive the anvil therebetween.

The present disclosure also relates to a system which includes a closure device comprising a first ring structure having a first distal portion and a first medial portion, a second ring structure having a second distal portion and a second medial portion, the first and second distal portions being movable between an open position, where the first and second distal portions form an angle relative to one another for receiving target tissue therebetween, and a closed position, where the first and second distal portions are drawn toward one another for gripping the target tissue, and an anvil about which the first and second medial portions are formed, wherein either one of proximal motion of the anvil relative to the first and second rings or proximal motion of the medial portions relative to the anvil causes the first and second distal portions to move into either one of the open position or the closed position; a flexible control member coupled to one of the anvil and the first and second rings to move the closure device between the open and closed position; and a cap configured to be attached to a distal end of an endoscope, the cap including a recess within which the closure device is seated.

In an embodiment, the closure device has a stem attached to a first proximal portion of the first ring and a second proximal portion of the second ring, the control member extending through the stem, the stem being sized and shaped to be received within a working channel of the endoscope, the member having a failure point proximal to the stem and a loop at a distal end thereof extending around the anvil such that proximal movement of the member moves the anvil proximally.

In an embodiment, the system further includes a grasper having a pair of grasping jaws configured to move the first and second distal portions between the open and the closed positions and a shaft extending from a proximal end of the pair of grasping jaws through the working channel of the endoscope.

In an embodiment, the anvil has a length greater than a diameter of the cap.

Furthermore, the present disclosure relates to a method for grasping tissue which includes mounting a closure device on a cap; attaching the cap to a distal end of an endoscope, the closure device comprising a first ring structure having a first distal portion and a first medial portion, a second ring structure having a second distal portion and a second medial portion, the first and second distal portions being movable between an open position, where the first and second distal portions form an angle relative to one another for receiving target tissue therebetween, and a closed position, where the first and second distal portions are drawn toward one another for gripping the target tissue, and an anvil about which the first and second medial portions are formed; moving proximally one of the anvil and the first and second rings relative to the other one of the anvil and the first and second rings to move the first and second distal portions between the open position or the closed position.

In an embodiment, the method further includes locking the anvil relative to the first and second rings to lock the first and second rings in the closed position.

In an embodiment, the closure device has a stem attached to a first proximal portion of the first ring and a second proximal portion of the second ring, a control member extending through the stem, the stem being sized and shaped to be received within a working channel of the endoscope, the member having a failure point proximal to the stem and a loop at a distal end thereof extending around the anvil.

In an embodiment, drawing the member proximally moves the anvil proximally relative to the first and second rings and drawing the member further proximally increases tension on the member until the failure point fails and the closure device separates from the cap and the endoscope.

In an embodiment, a grasper having a pair of grasping jaws and a shaft extending from a proximal end of the pair of grasping jaws through a working channel of the endoscope moves the first and second distal portions between the open and closed positions.

BRIEF DESCRIPTION

DETAILED DESCRIPTION

The present disclosure may be further understood with reference to the following description and the appended drawings, wherein like elements are referred to with the same reference numerals. The present disclosure relates to devices for closing, e.g. clipping target tissue. As described herein, the term "clip" or "clipping device" refers to devices configured to lock into a closed position around target tissue during an interventional procedure, e.g. to stanch blood flow, and which are left in the body after actuation. Certain of the exemplary embodiments may also relate to devices for gripping, e.g. "clamping" tissue during interventional procedures, e.g. to approximate tissue for suturing by a further device, which are not locked into a closed position and may be opened and removed from the body before the procedure is completed. Devices operable for either one or both of clipping/clamping may be referred to as "closure devices."

Each of the devices has two rings actuatable between an open position and a closed position relative to one another. In some embodiments, the rings are initially biased toward the closed position and actuating the device spreads the rings, while in other embodiments the rings are initially biased toward the open position and actuating the device draws the rings together. Each of the devices described herein has an actuation mechanism that may operate the opening/closing multiple times, i.e., that is operable to both open and close as many times as deemed necessary by the operating physician to correct a position at which the closure force is applied. Some of the embodiments described herein, e.g. for clipping devices, are configured so that the rings may be locked together in the closed position when the operating physician determines that the placement of the clip is correct.

Certain of the embodiments described herein have components that are mountable within a distal end of a working channel of an endoscope to hold the apparatus in a desired position against a distal end of an endoscope, while others are mountable to an exterior of the distal end of the endoscope, and still others are extended distally beyond a working channel of the endoscope and have a connection therein without direct mounting to the endoscope. An actuator, i.e. a user interface for the actuation mechanism, at the handle of the endoscope generally provides an actuation tension via pull wire to operate the closure device.

In some embodiments, when the device is mounted to the endoscope, the endoscope may provide a load bearing surface to resist a proximally directed force due to the tension applied to the pull wire so that the actuation load operates to move the rings into a desired opposite position (open or closed) relative to one another from an initial position toward which they are biased (i.e., a position to which the rings revert when no actuating force is applied to the pull wire). As will be described below, the endoscope-mounted embodiments are generally directly actuated by a pull wire, while the unmounted embodiments are actuated by a grasper or similar device.

As will be described in further detail below, each of the embodiments has a closure aspect comprising two rings. The two rings are joined via a connecting linkage that may vary between embodiments. For example, some embodiments comprise proximal portions of the rings that are welded or otherwise joined together, while other embodiments are connected by medial struts. A medial portion of each of the rings is disposed around or adjacent to an anvil, e.g. a wedge, a rod, a pin, a divider, etc. that acts as a pivot point about which the rings deform or rotate. Each of the devices is actuated in one of a plurality of ways.

In some embodiments, the anvil may be translated, e.g. drawn proximally, by a pull wire causing the medial portions of the rings to elastically deform about the anvil forcing the rings into a position (i.e. open or closed) different than the initial position. In other embodiments, a portion of one or both of the rings positioned proximal to the anvil is translated, e.g. drawn proximally, by a pull wire, elastically deforming medial portions of the rings around a stationary anvil and forcing the rings into a different position. In still other embodiments, a grasper or similar device translates a proximal portion of one or both of the rings relative to the anvil which acts as a pivot point forcing a distal portion of one or both of the rings into a different position.

Figure 1:
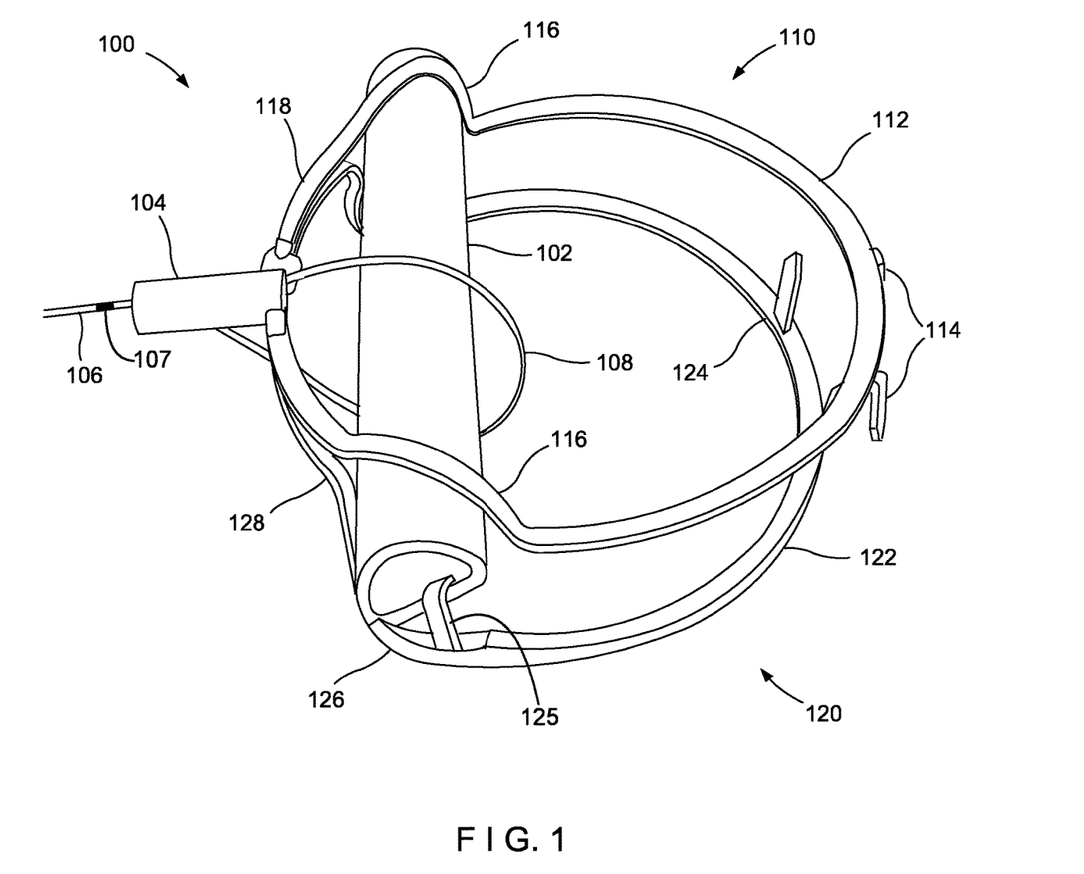
FIG. 1 shows a closure device according to a first exemplary embodiment biased in a naturally closed position.
Figure 2:
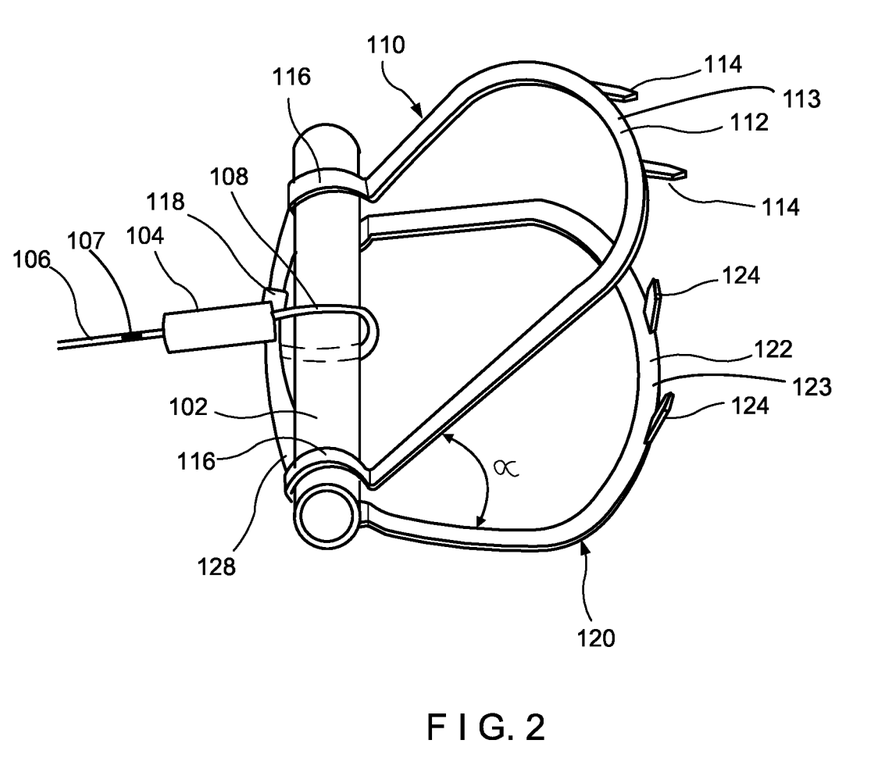
FIG. 2 shows the closure device of FIG. 1 actuated into an open position.

FIGS. 1-2 shows a closure device 100 according to a first exemplary embodiment comprising a first ring 110 and a second ring 120 with medial portions 116, 126 formed about an anvil 102 so that gripping distal portions 112, 122 of the rings 110, 120 are biased toward a naturally closed position. In the present embodiment, each of the gripping portions 112, 122 has an open center hole. One or both of the gripping portions 112, 122 (in this embodiment, both) comprises teeth 114, 124 extending from an inner surface of the corresponding gripping portion toward the other of the gripping portions 112, 122 so that target tissue may be gripped therebetween. However, in other embodiments, the gripping ends 112, 122 may have no teeth, or may comprise plates instead of center holes, to be described further below.

In the present embodiment, the gripping portions 112, 122 of the first and second rings 110, 120 are substantially flat and parallel to one another while in the naturally biased closed position, as seen in FIG. 1. The gripping portions 112, 122 are semi-circular, however other shapes may be used. The gripping portions 112, 122 may be offset by a given distance, depending on the size of the target tissue to be gripped. In other words, a distal end 113 of the gripping portion 112 extends distally beyond a distal end 123 of the gripping portion 122.

In this embodiment, the gripping portion 112 of the first ring 110 is shown to extend further distally than the gripping portion 122 of the second ring 120. However, in other embodiments, the rings 110, 120 may substantially mirror one another, i.e. have a same longitudinal extension, or be offset from one another differently than shown in the present embodiment. In embodiments where the rings 110, 120 have teeth 114, 124, the rings 110, 120 should be arranged so that the teeth 114, 124 are offset from one another, i.e. not interfere with one another, when the rings 110, 120 are in the closed position.

The first ring 110 defines a pair of medial portions 116 adjacent to the anvil 102 that cooperate with a corresponding pair of medial portions 126 of the second ring 120 to form a detent within which the anvil 102 resides when in the closed position. That is, the medial portions 116, 126 of the rings 110, 120 define a space sized and shaped to receive the anvil 102 therein so that, when the anvil 102 resides in this space, the rings 110, 120 are substantially parallel to one another in a desired position so that the teeth 114 and 124 will grip tissue trapped therebetween.

The medial portions 116 of the first ring 110 are formed with a curvature that extends around and partially matches a curvature of the anvil 102 (in this embodiment the anvil 102 is at least partially cylindrical). The medial portions 126 of the second ring 120 are also shaped to receive the anvil 102 and may be symmetric with or differently shaped from the medial portions 116 of the first ring 110. In this embodiment, the medial portions 126 are separated from the anvil 102 a given distance, then curve and extend toward the first ring 110 at positions proximal to the anvil 102. In addition, each of the medial portions 126 includes a slider bar 125 engaging an end of the anvil 102 to maintain the anvil 102 centered between the first and second rings 110, 120. Those skilled in the art will understand that the slider bars 125 may be placed on either of the first and second rings 110. 120 as desired.

Proximal to the medial portions 116, 126 are the proximal portions 118, 128 of the rings 110, 120, which are tightly spaced until meeting at a proximal-most point. The proximal portions 118, 128 are held together in any desired manner. For example, the proximal portions 118, 128 may be coupled to one another by being crimped or welded to one another or otherwise joined at this proximal position or by being coupled to the stem 104 in any known manner. Although a particular shape for each of the rings 110, 120 has been described, other curvatures and spacings for the medial portions 116, 126 and proximal portions 118, 128 may be used without departing from the scope of the disclosure.

The anvil 102 in this embodiment is a partially cylindrical rod having a diameter greater than the spacing between the proximal portions 118, 128 of the rings 110, 120 when the rings 110, 120 are closed. The anvil 102 may be joined to the rings 110, 120 in various ways so that the anvil 102 remains situated between the rings 110, 120 but may move proximally and distally relative thereto. In other words, the anvil 102 may be joined to the rings 110, 120 so that it does not slide out from between the rings 110, 120. For example, the anvil 102 may be shaped in a way to prevent sliding, i.e. may have a shape that is not uniformly cylindrical. The anvil 102 may change diameter so that the diameter is reduced at the location where the rings 110, 120 cross the anvil 102, effectively preventing the larger diameter remainder of the anvil 102 from sliding past the rings 110, 120.

The rings 110, 120 are shaped so that drawing the anvil 102 proximally relative to the rings 110, 120 brings the anvil 102 into contact with the tightly spaced proximal portions 118, 128 forcing the rings 110, 120 to separate, as seen in FIG. 2, and bring the closure device 100 into the open position. In the present embodiment, the distal portions 112, 122 of the rings 110, 120 preferably open to an angle α (between the first and second rings 110, 120) of between 45 and 180 degrees, or more specifically, between 75 and 100. Those skilled in the art will understand that the angle α is chosen to ensure that, in the open position, the distal ends 113, 123 of the first and second rings 110, 120, respectively, are separated from one another by a gap sufficient to receive a desired portion of target tissue therebetween for gripping and, although this angle may vary between the various embodiments the same angular ranges apply to all of the disclosed embodiments. In some embodiments, only one of the two rings 110, 120 may open relative to the other of the two rings 110, 120, while in other embodiments, both of the rings 110, 120 may open away from one another.

The point at which the rings 110, 120 are joined, e.g. the weld, has a stem 104 joined thereto through which a pull wire 106 is extended. The pull wire 106 has a loop 108 extending around the anvil 102 so that proximal motion of the pull wire 104 draws the anvil 102 proximally therewith. The stem 104 may be snugly received in the working channel of an endoscope or within a channel running outside the scope or otherwise stably held in a desired position on the distal end of the endoscope as would be understood by those skilled in the art. When an actuation force is applied to the device 100, the endoscope against which the device 100 is held provides a resistive force to offset the actuation load. For example, the pull wire 106 may extend proximally through the endoscope (e.g., through a working channel of the endoscope) to exit the handle of the endoscope via a port, or may be connected to a feature on the handle allowing the pull wire 106 to be easily pulled proximally to apply tension or to be locked in a desired location to maintain a desired state of the device.

For example, the feature on the handle may comprise a reel to take up the slack of the pull wire 106, a lever, a rotary knob, a plunger, etc. As tension is applied to the pull wire 106, the device is drawn proximally against the endoscope increasing tension on the pull wire 106 and drawing the anvil 102 proximally between the rings 110, 120 to move the device to the open position. As long as tension is maintained on the pull wire 106, the anvil 102 is held between the proximal portions 118, 128 keeping the device in the open position. The tension may be applied manually, or there may be a locking feature at the handle for maintaining the pull wire at a desired tension.

When tension is released from the pull wire 106 (e.g., when the device has been positioned with desired tissue to be gripped between the rings 110, 120), the natural bias of the rings 110, 120 draws the rings 110, 120 together forcing the anvil 102 back into the space between the medial portions 116, 126 returning the device to the closed position gripping the desired tissue. A manual lock may engage when the anvil 102 is allowed to move to a fully closed position so that, when the clip is locked over desired tissue, proximal tension may be applied to the pull wire 106 until a predetermined failure point 107 (e.g., a weakened portion of the pull wire 106) is severed releasing the clip from the pull wire 106. For example, tabs on the one or both rings 110, 120 may engage a proximal side of the anvil 102 when the anvil 102 moves to a distal-most position corresponding to the fully closed configuration.

Because the device 100 is naturally biased in the closed position, when the rings 110, 120 are positioned at a desired location on the target tissue, the pull wire 106 may be severed and the device 100 will remain on the target tissue until it sloughs off of the target tissue at a later time. The devices described that have a naturally closed bias do not need a further mechanism for locking the device 100 closed, whereas those devices described later that have a naturally open bias, and are intended to remain in a closed position on target tissue after the device is positioned thereon, have a further mechanism for locking the device closed.

Figure 3:
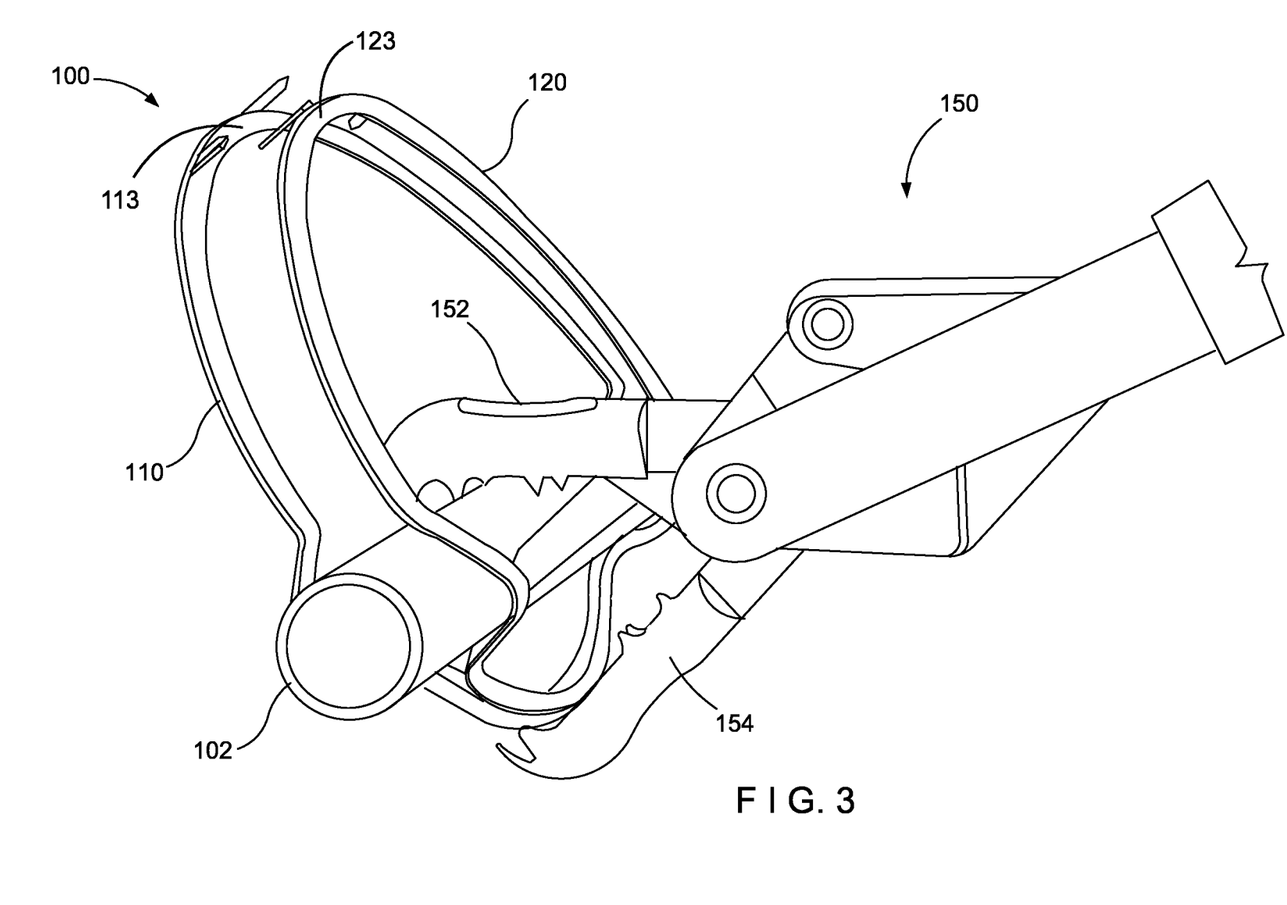
FIG. 3 shows the closure device of FIG. 1 with a secondary device for actuating the closure device.
Figure 4:
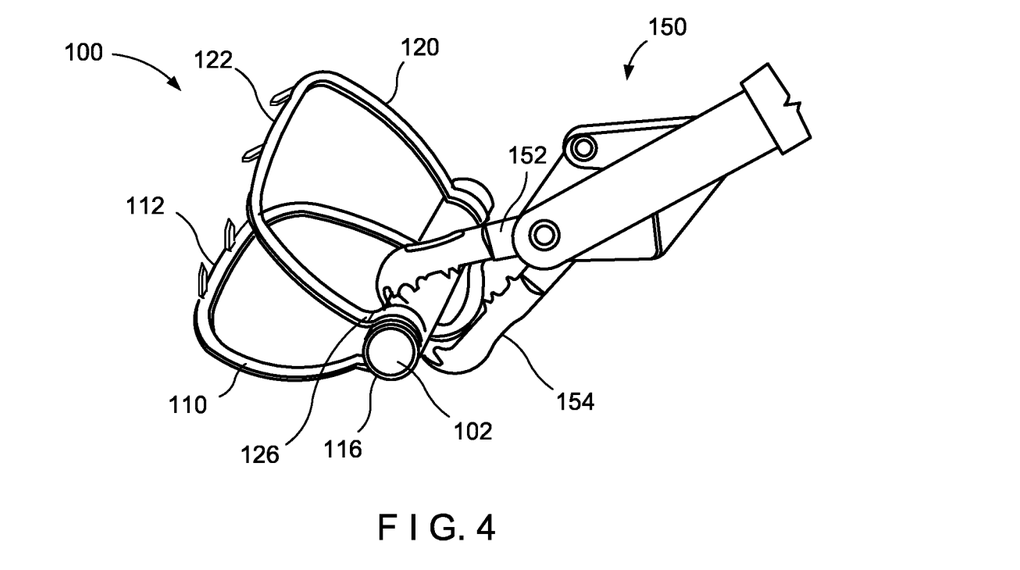
FIG. 4 shows the closure device of FIG. 1 actuated into the open position with the secondary device of FIG. 3.

In alternate embodiments, rather than having a stem 104 facilitating the use of a pull wire 106 joined to proximal portions of the rings 110, 120, the closure device 100 may utilize a secondary tool to actuate the rings 110, 120. For example, as shown in FIGS. 3-4, a grasper 150 may be used to pull the anvil 102 from a distal position in which the rings 110, 120 are closed, to a proximal position in which anvil forces the rings 110, 120 apart against their natural bias to the open tissue receiving configuration. As would be understood by those skilled in the art, the rings 110, 120 of this embodiment and the anvil 102 are formed substantially similarly to the rings 110, 120 and the anvil 102 of the embodiment of FIG. 1.

As would be understood by those skilled in the art, many types of grasper or grasping tool may be used. The exemplary grasper 150 has first and second grasping halves 152, 154, respectively. In one method of use, the first grasping half 152 may be positioned against a distal facing portion of the anvil 102 while the second grasping half 154 is positioned against a proximal edge of the proximal portions 118, 128 of the rings 110, 120 so that as the grasper 150 is closed (i.e., the grasping halves 152, 154 are drawn together), the anvil 102 is drawn proximally between the proximal portions 118, 128 forcing the device 100 into the open position. When the grasping halves 152, 154 are allowed to separate from one another, the rings 110, 120 will be drawn together by their natural bias forcing the anvil 102 distally into the space between the medial portions 116, 126 returning the device to the closed position.

FIG. 3 shows the grasper 150 in an open position with the closure device 100 gripped within the first and second grasping halves 152, 154 but not yet actuated, while FIG. 4 shows the grasper 150 in a closed position with the first and second grasping halves 152, 154 drawn together and the anvil 102 forced from the distal position to the proximal position between the rings 110, 120, forcing the gripping ends of the rings 110, 120 apart from one another into the open position. Although a grasper 150 is described, other secondary devices operable to grip the device 100 and bring the anvil 102 proximally relative to the rings 110, 120 may be used. When the secondary device is used, the closure device 100 need not be coupled directly to the endoscope. The secondary device may be extended through the working channel of the endoscope and may internally provide the actuation force and resistive force needed to open the closure device 100 as with known graspers while the closure device 100 need only be held in place so that, as a force is applied thereto via the secondary device, the anvil 102 may be moved relative to the rings 110, 120.

The present configuration allows the closure device 100 to secure target tissue between the gripping portions 112, 122, to approximate and/or compress the target tissue to e.g. stem blood flow through an opening in the target tissue, bring the tissue together for suturing, or to approximate or compress tissue for any other reason. The open ring configuration allows tissue adjacent to the portion gripped by the gripping portions 112, 122 to expand between the center holes of the gripping portions 112, 122 of the rings 110, 120 when the gripping portions 112, 122 are closed onto the target tissue.

In another embodiment, the gripping portions 112, 122 comprise plates instead of having open center holes. This configuration compresses all tissue between the plates and forces tissue adjacent to this compressed tissue to move outward from edges of the plates via an open side of the ring configuration. This arrangement permits tissue forced out of the plates to then be treated (e.g., resected via a secondary tool) as would be understood by those skilled in the art.

Figure 5:
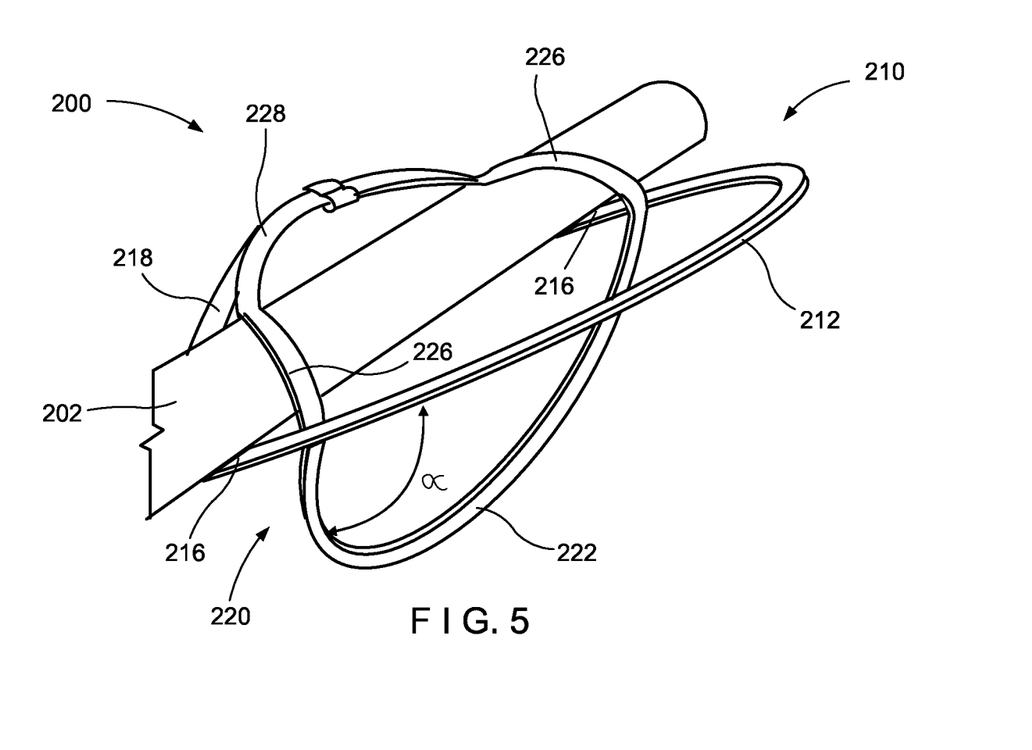
FIG. 5 shows a closure device according to a second exemplary embodiment biased in a naturally open position.
Figure 6:
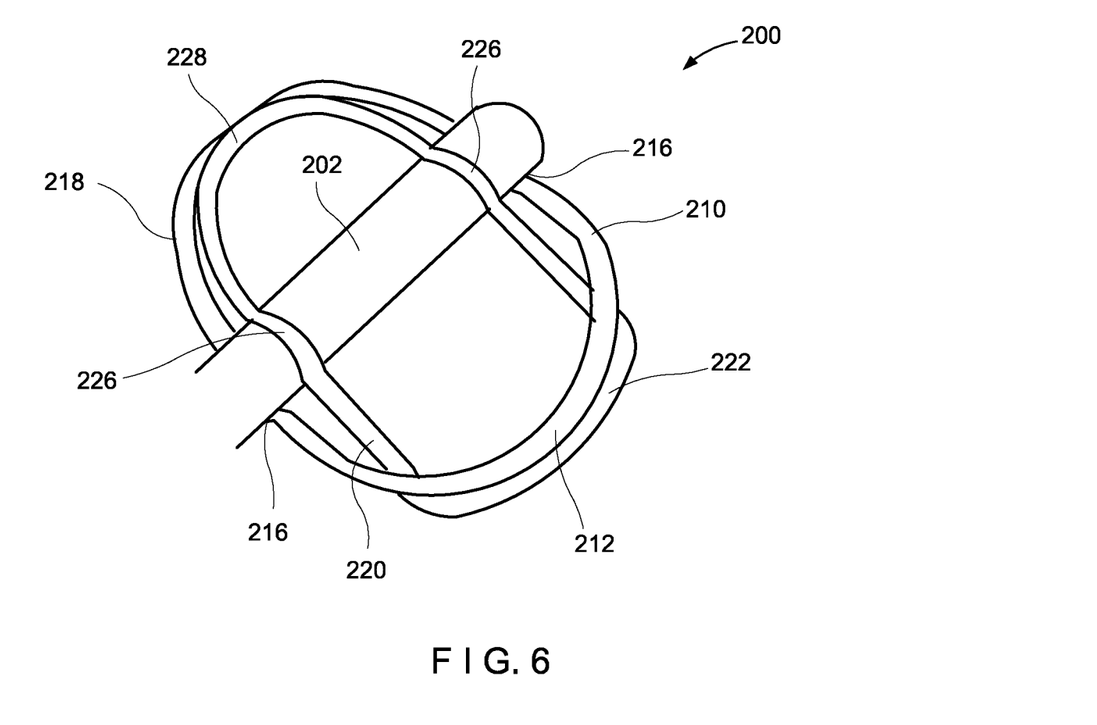
FIG. 6 shows the closure device of FIG. 5 actuated into a closed position.
Figure 11:
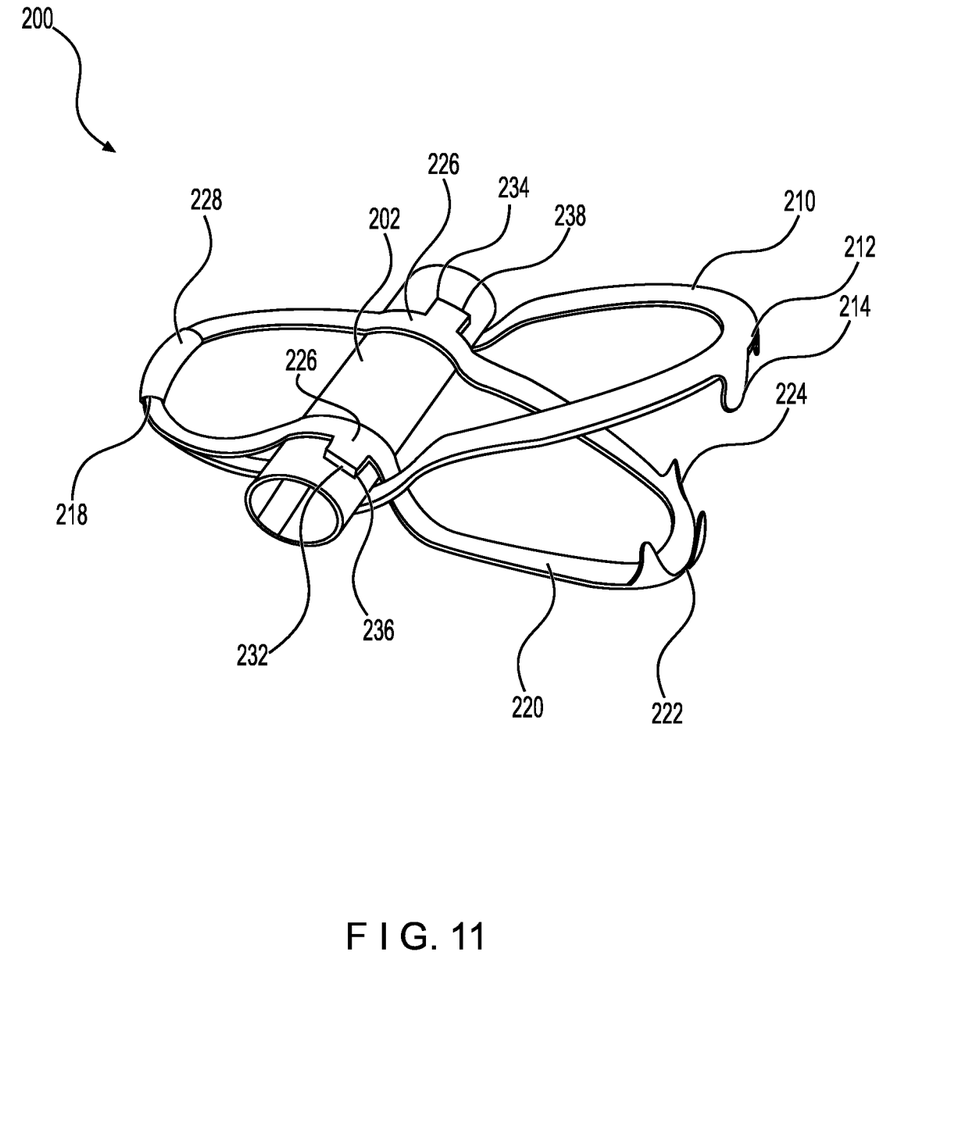
FIG. 11 shows an embodiment of the closure device of FIG. 5 including a locking mechanism.

FIGS. 5-6 shows a closure device 200 according to a second exemplary embodiment comprising a first ring 210 and a second ring 220 having medial portions 216, 226 with an anvil 202 received therebetween so that the gripping distal portions 212, 222 of the rings 210, 220 may be moved between an open position and a closed position. In this embodiment, the rings 210, 220 are biased toward a naturally open position, as shown in FIG. 5. In the present embodiment, the gripping portions 212, 222 have open center holes and do not include teeth. However, in other embodiments (as shown in FIG. 11), the gripping portions 212, 222 may include inward-facing teeth 214, 224 similar to those teeth 114, 124 described above with regard to closure device 100, or may comprise plates instead of center holes, as described above.

In the present embodiment, the first and second rings 210, 220 are formed to create a natural bias so that the gripping portions 212, 222, when not acted on by an outside force, move to an open position in which they are angled relative to one another so that the distal ends of the rings 210, 220 are spaced apart from one another. As indicated above, the range of an angle between the first and second rings 210, 220 is preferably selected to be sufficiently large to permit a target portion of tissue to be gripped to be received between the distal ends of the rings 210, 220.

Those skilled in the art will understand that tissue may be drawn between the gripping elements of any of the embodiments described herein using any known methods or devices (e.g., suction, graspers, etc.). Each of the gripping portions 212, 222 extends substantially straight (along a curved path within a single plane) with these planes angled relative to one another and intersecting adjacent to the medial portions 216, 226 each of which curves out of the plane of the distal portion of its corresponding gripping portion 212, 222 around opposite sides of the anvil 202 which is received between the gripping portions 212, 222.

In this embodiment, because the planes in which the gripping portions 212, 222 intersect is distal to the medial portions 216, 226, the medial portion 216 passes on a side of the anvil 202 opposite a side on which the distal end of the corresponding gripping portion 212 extends and similarly for the medial portion 226 and its corresponding gripping portion 222. That is, as can be seen in FIG. 5, the gripping portion 212 of the first ring 210 extends above the anvil 102 while the medial portion 216 passes below the anvil 202. Similarly, the gripping portion 222 of the first ring 210 extends below the anvil 202 while the medial portion 226 passes above the anvil 202. The medial portions 216, 226 curve around the anvil 202 with a partial curvature selected, in this embodiment, to substantially match a curvature of a portion the anvil 202 which will be in contact with the corresponding medial portion in a manner similar to that described for the medial portions 116, 126 of the closure device 100 relative to the anvil 102. The proximal portions 218, 228 of the rings 210, 220 are tightly spaced until meeting at a proximal-most point at which the rings 210, 220 are connected, e.g., welded, in a manner similar to the closure device 100.

Unlike the closure device 100, the closure device 200 is actuated by drawing the proximal portions 218, 228 of the rings 210, 220 proximally, rather than by drawing the anvil 202 proximally. As may be seen more clearly in FIG. 6, drawing the proximal portions 218, 228 of the rings 210, 220 proximally causes the gripping portions 212, 222 to angulate until they are brought nearly parallel to one another—i.e., until distal ends of the gripping portions 212, 222 approach one another in a closed position. The curvature of the medial portions 216, 226 is such that when the proximal portions 218, 228 are drawn proximally, inner surfaces of the medial portions 216, 226 on the distal side of the anvil 202 facing the anvil 202 are brought into contact with the anvil 202. This contact, in combination with the proximal force, acts to angulate the medial portions 216, 226 which in turn brings the distal portions 212, 222 toward one another.

Similarly to the closure device 100, the closure device 200 may comprise a stem for mating the closure device 200 to the working channel of an endoscope. A secondary device may also be used to actuate the closure device 200, however, the secondary device must be operable to spread the anvil and the proximal portions 218, 228 apart from one another, rather than pushing them closer together.

The device 200 may include a locking mechanism for locking the rings 210, 220 in the closed position. As shown in FIG. 11, the anvil 202 includes at least one mechanical feature that is sized and shaped to engage a corresponding mechanical feature on at least one of the rings 210, 220. In the exemplary embodiment, the anvil 202 includes a first locking window 232 at a first end and a second locking window 234 at a second end. The first locking window 232 is configured to engage a front locking tab 236 extending from the medial portion 226 and the second locking window 234 is configured to engage a rear locking tab 238 extending from the medial portion 226.

When the rings 210, 220 are positioned in a location corresponding to a locking position, the locking tabs 236, 238 align with the locking windows 232, 234, therefore locking the rings 210, 220 relative to the anvil 202. In other words, when the proximal portions 218, 228 are drawn proximally a predetermined distance, the locking tabs 236, 238 slide into the locking windows 232, 234 to lock the rings 210, 220 in the closed position. When in the closed position, the angle between the first and second rings 210, 220 is preferably selected to be less than 20 degrees. Although the locking mechanism is described above relative to the closure device 200, one skilled in the arts will understand that the locking mechanism may be used with all the exemplary embodiments. As those skilled in the arts will understand, embodiments of the closure device where the anvil is moved proximally relative to the rings (e.g., the closure device 100), the locking mechanism has mechanical features on the anvil positioned to align with corresponding mechanical features on the rings to lock the closure device in the closed position.

Figure 7:
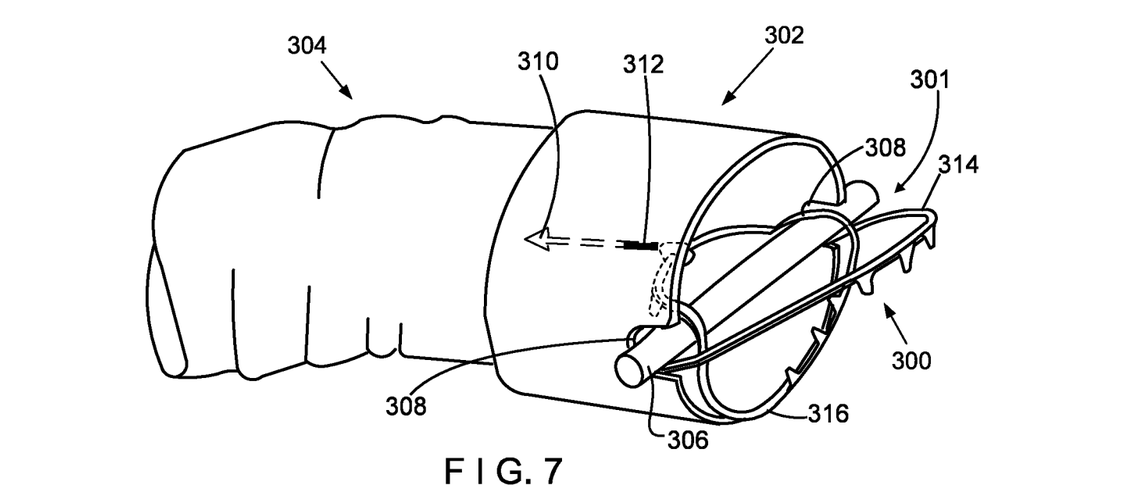
FIG. 7 shows a closure device mounted to a cap and coupled to an endoscopic shaft.

In another embodiment, the closure system 300 includes a clipping device 301 mounted on a cap 302 configured to be mounted over the distal end of an endoscope 304 or other insertion instrument. FIG. 7 shows the clipping device 301 mounted on the cap 302 with an anvil 306 thereof received in diametrically opposed recesses 308 of the cap 302. The cap 302 is sized and shaped so that it may slid over the distal end of an endoscope 304 while remaining out of the way of the optics and working channel of the endoscope 304 as would be understood by those skilled in the art. A pull wire 310 extending through the working channel of the endoscope 304 is coupled to the proximal portions of the rings of the device 301 and includes a failure point 312 as described above. The anvil 306 is positioned between first and second rings 314, 316 of the device 301 so that, as the pull wire 310 is pulled proximally, the first and second rings 314, 316 are drawn proximally over the anvil 306 (which is held in position by the cap 302) drawing the first and second rings 314, 316 toward each other into the closed position to grip tissue received therebetween.

As with prior embodiments, when the first and second rings 314, 316 have been drawn to the fully closed configuration, drawing the pull wire 310 further proximally (e.g., via an actuator on a proximal handle that remains outside the body accessible to a user) increases tension on the pull wire 310. During this proximal retraction of the pull wire 310, the anvil 306 is locked mechanically in the closed position (e.g., by tabs on one or both of the rings 314, 316 which, once positioned distally of the anvil 306 prevent the anvil 306 from moving distally therepast). Once, the device 301 has been mechanically locked in the closed position, drawing the pull wire 310 further proximally increases the tension on the pull wire 310 until the failure point 312 fails separating the device 301 from the pull wire and permitting the endoscope 304 including the cap 302 to be withdrawn from the body while leaving the device 301 within the body clipped over target tissue.

The device 300 shown in FIG. 7 has an anvil 306 with a length greater than a diameter of the cap 302 (or of the portion of the cap 302 traversed by the anvil 306 when it is received in the recesses 308) so that the anvil 306 can be securely seated in the recesses 308. However, the anvil 306 may have a length substantially equal to the separation between the recesses 308 so that the ends of the anvil 306 do not protrude beyond the outer profile of the cap 302.

Figure 8:
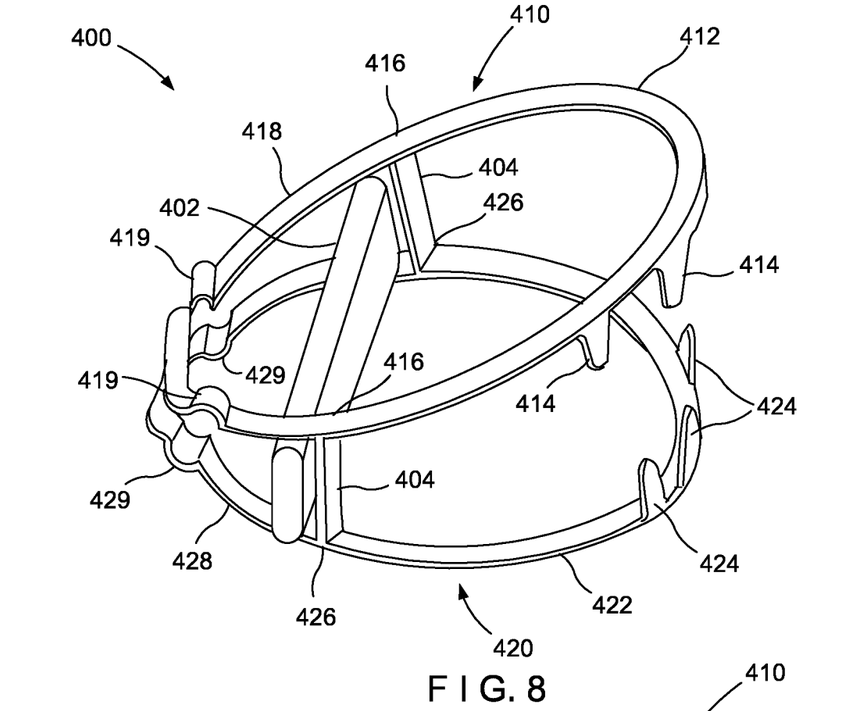
FIG. 8 shows a closure device according to a third exemplary embodiment biased in a naturally open position and having features for locking closed.
Figure 9:
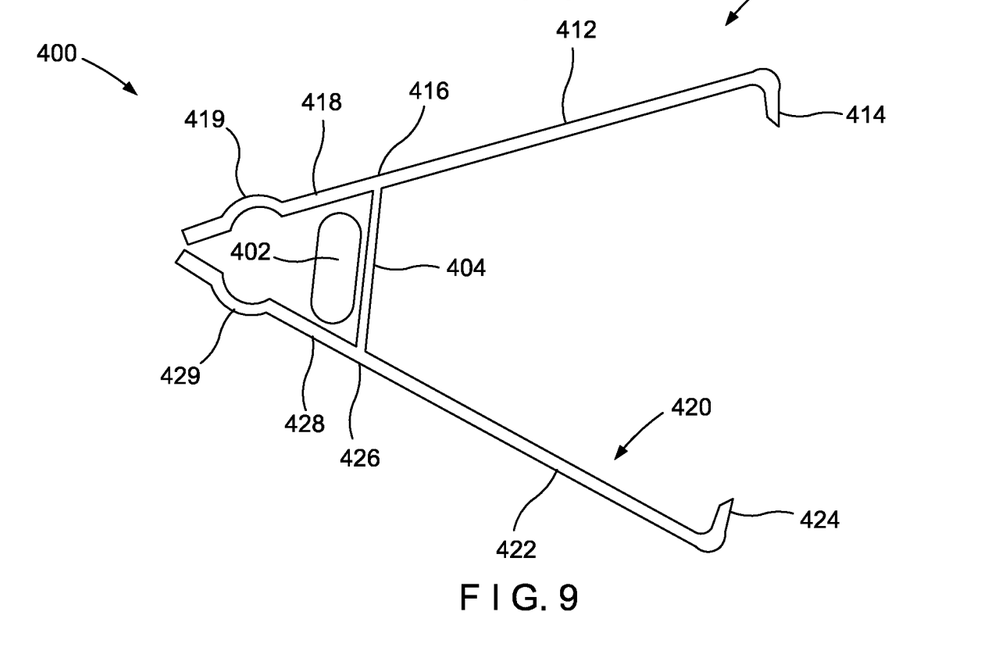
FIG. 9 shows a side view of the closure device of FIG. 8 in an open position.
Figure 10:
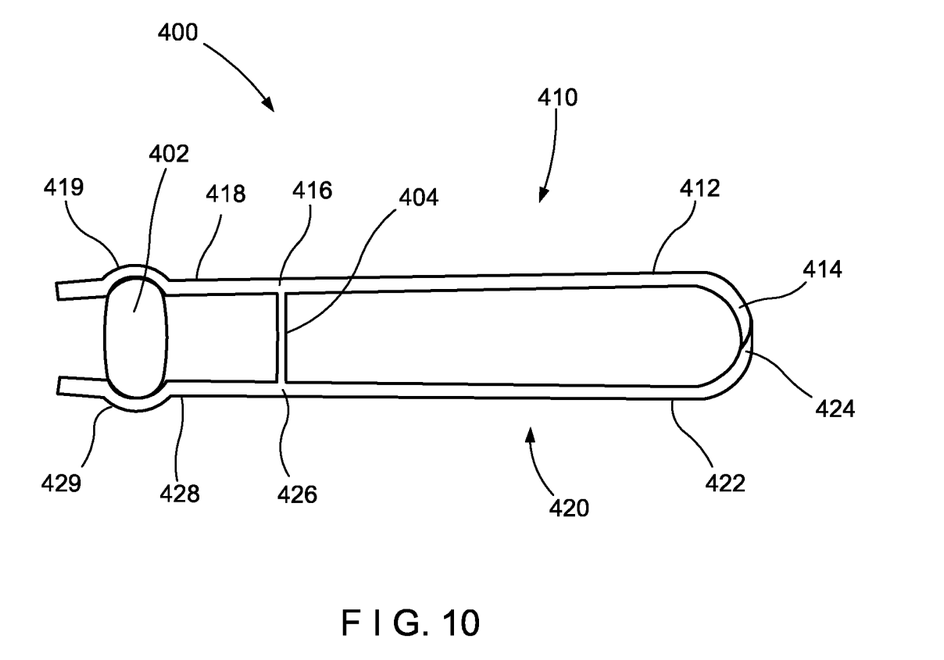
FIG. 10 shows a side view of the closure device of FIG. 8 in a closed position.

FIGS. 8-10 show a closure device 400 according to a third exemplary embodiment comprising a first ring 410 and a second ring 420 joined by two flexible connecting struts 404 configured to establish an angle between the rings 410, 420 based on a position of an anvil 402 proximal to the struts 404. Unlike the previously described embodiments, the rings 410, 420 of the closure device 400 are not formed with a curvature extending around an initial position of the anvil 402. Rather, each of the rings 410, 420 is substantially planar, with the exception of proximal recesses 419, 429 to be explained further below.

The rings 410, 420 of the closure device 400 may be substantially symmetrical with the exception of a placement of teeth 414, 424 on the distal ends of the distal portions 412, 422, which may have an offset relative to the teeth of the opposing ring so as to not interfere with one another when the device 400 is in the closed position. However, substantial symmetry is not required. The connecting struts 404 are located at and form a bridge between positions 416, 426 on the rings 410, 420, the positions 416, 426 being proximal to a centerline of the rings 410, 420. The distal portions 412, 422 of the rings 410, 420 distal to the positions 416, 426 may be used for gripping target tissue.

The device 400 is shaped so that the rings 410, 420 are naturally splayed in an open position. That is, the rings 410, 420 are biased to assume an open position in which distal ends thereof are separated from one another and force must be applied to move the device 400 to the closed position in which the distal ends of the rings 410, 420 are drawn into proximity to one another to grip tissue therebetween. Thus, the proximal portions 418, 428 of the rings 410, 420 proximal to the positions 416, 426 where the connecting struts 404 are located are naturally angled toward one another. The anvil 402, when the rings 410, 420 are in the open position, is located adjacent to the connecting struts 404.

In a manner similar to the device 100 described above, the anvil 402 may be drawn proximally relative to the rings 410, 420 by means of a pull wire (not shown) or via a separate device. Drawing the anvil 402 proximally brings the anvil 402 into contact with progressively more proximal portions of the inner surfaces of the proximal portions 418, 428 of the rings 410, 420 and spreads the proximal portions 418, 428 apart from one another, which in turn closes the distal portions 412, 422 as each of the rings 410, 420 rotates substantially about an axis defined by the points at which the connecting struts 404 couple to the corresponding ring 410, 420.

The proximal portions 418, 428 include recesses 419, 429 shaped to receive the anvil 402 therebetween so that, when the anvil 402 has been drawn proximally relative to the rings 410, 420, sufficient to bring the rings 410, 420 to the closed position, the anvil 402 snaps into the recesses 419, 429 and the device 400 is locked in the closed position as the bias of the rings 410, 420 secures the anvil 402 in the recesses 419, 429. In operation, the device 400 may have three configuration states: open, closed, and locked. Prior to locking the device 400, the operating physician may bring the device 400 between the open position and closed position multiple times. When the physician has confirmed that a currently closed positioning of the device 400 on target tissue is correct, the anvil 402 may be drawn further distally to lock the device 400 closed by snapping the anvil 402 into the recesses 419, 429.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

The invention claimed is:

1. A method for grasping tissue, comprising:
mounting a closure device on a cap;
attaching the cap to a distal end of an endoscope, the closure device comprising a first ring structure having a first distal portion and a first medial portion, a second ring structure having a second distal portion and a second medial portion, the first and second distal portions being movable between an open position, where the first and second distal portions form an angle relative to one another for receiving target tissue therebetween, and a closed position, where the first and second distal portions are drawn toward one another for gripping the target tissue, and an anvil about which the first and second medial portions are formed; and
moving proximally one of the anvil and the first and second rings ring structures relative to the other one of the anvil and the first and second rings ring structures to move the first and second distal portions between the open position or the closed position.

2. The method of claim 1, further comprising:
locking the anvil relative to the first and second ring structures to lock the first and second ring structures in the closed position.

3. The method of claim 1, wherein the closure device has a stem attached to a first proximal portion of the first ring structure and a second proximal portion of the second ring structure, a control member extending through the stem, the stem being sized and shaped to be received within a working channel of the endoscope, the member having a failure point proximal to the stem and a loop at a distal end thereof extending around the anvil.

4. The method of claim 3, wherein drawing the member proximally moves the anvil proximally relative to the first and second ring structures and drawing the member further proximally increases tension on the member until the failure point fails and the closure device separates from the cap and the endoscope.

5. The method of claim 1, wherein a grasper having a pair of grasping jaws and a shaft extending from a proximal end of the pair of grasping jaws through a working channel of the endoscope moves the first and second distal portions between the open and closed positions.

6. The method of claim 1, wherein the closure device has flexible connecting struts adjacent to the anvil and extending between the first medial portion of the first ring structure and the second medial portion of the second ring structure, first recesses adjacent to a first proximal portion of the first ring structure, and second recesses adjacent to a second proximal portion of the second ring structure, wherein the first and second recesses are sized and shaped to receive the anvil therebetween.

7. The method of claim 6, wherein moving the anvil proximally relative to the first and second ring structures moves the first and second distal portions into the closed position.

8. The method of claim 1, wherein the first and second ring structures have a curvature at each of the first and second medial portions sized and shaped to receive the anvil therebetween.

9. The method of claim 1, further comprising:
maintaining the anvil at a desired position between the first and second medial portions by engaging an end of the anvil with a protrusion extending from one of the first and second medial portions.

10. The method of claim 1, wherein the first and second ring structures are biased toward the closed position.

11. The method of claim 1, wherein the first and second ring structures are biased toward the open position.

12. The method of claim 1, wherein the closure device has a first gripping feature extending from one of the first distal portion and the second distal portion toward the other one of the first and second distal portions to grip the target tissue.

13. The method of claim 1, wherein a distal end of the first distal portion extends distally beyond a distal end of the second distal portion.

14. A method for grasping tissue, comprising:
mounting a closure device on a cap;
attaching the cap to a distal end of an endoscope, the closure device comprising a first tissue capture structure formed as a ring, the first tissue capture structure having a first distal portion and a first medial portion, and a second tissue capture structure having a second distal portion and a second medial portion, the first and second distal portions being movable between an open position, where the first and second distal portions form an angle relative to one another for receiving target tissue therebetween, and a closed position, where the first and second distal portions are drawn toward one another for gripping the target tissue, and an anvil about which the first and second medial portions are formed; and
moving proximally one of the anvil and the first and second tissue capture structures relative to the other one of the anvil and the first and second tissue capture structures to move the first and second distal portions between the open position or the closed position.

15. The method of claim 14, further comprising:
locking the anvil relative to the first and second tissue capture structures to lock the first and second tissue capture structures in the closed position.

16. The method of claim 14, wherein the closure device has a stem attached to a first proximal portion of the first tissue capture structure and a second proximal portion of the second tissue capture structure, a control member extending through the stem, the stem being sized and shaped to be received within a working channel of the endoscope, the member having a failure point proximal to the stem and a loop at a distal end thereof extending around the anvil.

17. The method of claim 16, wherein drawing the member proximally moves the anvil proximally relative to the first and second tissue capture structures and drawing the member further proximally increases tension on the member until the failure point fails and the closure device separates from the cap and the endoscope.

18. The method of claim 14, wherein the closure device has flexible connecting struts adjacent to the anvil and extending between the first medial portion of the first tissue capture structure and the second medial portion of the second tissue capture structure, first recesses adjacent to a first proximal portion of the first tissue capture structure, and second recesses adjacent to a second proximal portion of the second tissue capture structure, wherein the first and second recesses are sized and shaped to receive the anvil therebetween.

19. The method of claim 14, wherein moving the anvil proximally relative to the first and second tissue captures structures moves the first and second distal portions into the closed position.

20. The method of claim 14, further comprising:
maintaining the anvil at a desired position between the first and second medial portions by engaging an end of the anvil with a protrusion extending from one of the first and second medial portions.

* * * * *